United States Patent [19]

Hogle

[11] Patent Number: 5,199,441
[45] Date of Patent: Apr. 6, 1993

[54] FINE NEEDLE ASPIRATION BIOPSY APPARATUS AND METHOD

[76] Inventor: Hugh H. Hogle, 1627 Wasatch Dr., Salt Lake City, Utah 84108

[21] Appl. No.: 747,741

[22] Filed: Aug. 20, 1991

[51] Int. Cl.⁵ ............................................. A61B 10/00
[52] U.S. Cl. .................................. 128/753; 128/758; 604/272
[58] Field of Search ............... 128/753, 752, 751, 749, 128/750, 754, 755, 757, 758, 760, 763; 604/272, 274

[56] References Cited

U.S. PATENT DOCUMENTS

| | | | |
|---|---|---|---|
| 3,766,907 | 10/1973 | Muenzer | 128/749 |
| 4,194,513 | 3/1980 | Rhine et al. | 128/750 |
| 4,308,875 | 1/1982 | Young | 128/753 |
| 4,441,509 | 4/1984 | Kotsifas et al. | 128/757 |
| 4,757,826 | 7/1988 | Abdulhay | 128/757 |
| 4,799,494 | 1/1989 | Wang | 128/753 |
| 4,967,762 | 11/1990 | DeVries | 128/753 |
| 5,069,224 | 12/1991 | Zinnanti, Jr. | 128/752 |

Primary Examiner—Max Hindenburg
Assistant Examiner—Guy V. Tucker
Attorney, Agent, or Firm—J. Winslow Young

[57] ABSTRACT

A fenestrated, hollow needle mounted in fluid communication to a hollow hub, the hollow hub being mountable to a syringe or other suitable suction device for creating a negative pressure inside the hollow needle while it is inserted into tissue from which a biopsy sample is to be collected. The fenestrations are located adjacent the sharpened tip of the hollow needle and provide a significantly greater quantity of cells for the biopsy sample by scraping the cells from the tissue as the hollow needle in passing through the tissue. The diameter of the fenestrations are limited so as to inhibit tissue from being drawn through the fenestrations into a plugging relationship in the hollow needle. The hollow hub includes a reservoir for receiving the biopsy sample along with a pair of outwardly extending wings for improved and safer handling of the hollow hub.

14 Claims, 3 Drawing Sheets

FINE NEEDLE ASPIRATION BIOPSY APPARATUS AND METHOD

BACKGROUND

1. Field of the Invention

This invention relates to biopsy needles and, more particularly, to an improved fine needle aspiration biopsy needle apparatus and method for improved cell harvesting.

2. The Prior Art

Cytologic analysis is being increasingly utilized for the early detection of cancer or other abnormalities in the cellular structure of an organ such as a breast. The early detection of such cancers can be especially important. Studies have shown that cytologic analysis will reveal the presence of a precursor lesion, atypical ductal hyperplasia, several months before microcalcifications are detected during a standard mammography procedure. In one case, fine-needle aspirates revealed atypical ductal hyperplasia in three quadrants of the right breast one year before microcalcifications in that breast were detected by mammography. A second set of fine-needle aspirate samples was obtained at the time of the abnormal mammography; these revealed malignant cells in the same quadrant in which the abnormality was identified, as well as atypical hyperplasia in both the right and left breast. Subsequent biopsy revealed intraductal carcinoma, confirmed by histology. In the second case, the initial fine-needle aspirates showed atypical ductal hyperplasia in one breast concurrent with a suggestion of breast cancer in that breast on mammography. Breast cancer was subsequently confirmed by histology.

It has been hypothesized that in hereditary cancer, the initial alternation, or susceptibility to it, is inherited as a dominant gene, and that further mutational events cause lesion appearance and progression to malignancy. The analysis of the adenomatous polyp as the precursor for colon cancer is the most refined demonstration of a cancer precursor. Adenomatous polyps are known to be inherited, and deletions of tumor suppressors and activation of oncogenes in adenomatous polyps have been demonstrated in their conversion to malignancy. It is postulated that this process is analogous to the development of proliferative breast disease (PBD) and its conversion to breast cancer, except that PBD appears to be a more diffuse lesion. A recent study discusses PBD as an inherited disease and is reported in a scientific journal wherein I am one of the authors, *Science* Vol. 250, 21 Dec. 1990, pages 1715-1720, "Inheritance of Proliferative Breast Disease in Breast Cancer Kindreds."

From the foregoing it is clear that cytologic analysis of fine-needle aspirates is only as good as the aspirate obtained. Currently, aspirates are obtained from a breast, for example, using a 2.5 cm, 22-gauge needle mounted on a syringe. The syringe is used to apply a negative pressure of about 15 ml. The needle can also be attached to a syringe pistol for convenience in attaining the necessary negative pressure. Historically, the needle has been a conventional needle with a sharpened tip. The aspirate is obtained by the combination of the negative pressure and the cutting action of the sharpened tip. However, I have determined that the aspirate obtained by this standard technique is not consistently accurate in obtaining representative samples from the tissue into which the needle is inserted. This problem is extremely serious particularly in light of the high degree of reliance being placed on cytologic analysis as a cancer screening technique.

It is estimated that the false negative rate for the current state of the art biopsy needle is at least 15. The primary reason for this dangerously high false negative rate is directly related to the present design of the biopsy needle. In particular, aspirate from tissue obtained by conventional fine-needle aspiration biopsy techniques relies solely upon the cutting action of the sharpened end of the needle in combination with suction from inside the needle. Experience has shown that for some as yet unexplained reason, the aspirate obtained by this technique falls short of accurately representing the full range of cellular material through which the needle has passed. One possible explanation is that the cutting action of the needle dislodges a relatively large piece of noncritical tissue which temporarily blocks the needle from receiving additional aspirate from the surrounding tissue. This, in turn, means that the needle is not collecting aspirate during this portion of its traverse through the tissue.

Another possible theory is that the sharpened needle acts as a "corer" in that it cuts a core of tissue, the core having a length incrementally less than the distance of penetration of the needle in the tissue. Such a core is almost never obtained along the entire depth of penetration by the needle. Further, such a sample, if it were obtainable on a consistent basis would be too large an aspirate for accurate cytological examination. In any event, pathologists prefer free cells rather than tissue cores to conduct a proper cytological examination.

Needle cannulae are known in the art and are used for a number of medical applications including, for example, Anesthesiology, Angiography, Myelography, Roentgenography, and Ventriculography. As cannulae, these needles are specifically designed with relatively large single, double, or even triple holes, all of which are spaced from the pointed tip which is generally a closed point. If one were to attempt to use one of these needle cannulae as a biopsy needle there is a high probability that the relatively large holes in the sidewall would allow the suction inside the needle to pull the surrounding tissue into the lumen of the needle thereby temporarily plugging the needle against the further collection of aspirate.

Another disadvantage of the attempted adaptation of the prior art needle cannulae as a biopsy needle is absence of an aspirate collection reservoir in the hub as well as the lack of outwardly extending wings on the hub to assist in the safe, convenient handling of the needle. Further, since the needle cannulae are designed as cannulae, as the name implies, they do not include an indicia to indicate the withdrawal limit for the needle.

It would, therefore, be a significant advancement in the art to provide an improved needle apparatus and method for obtaining aspirates using fine-needle biopsy techniques. It would also be an advancement in the art to provide an improved biopsy needle for obtaining a more comprehensive aspirate from the tissue through which the needle is passed. Another advancement in the art would be to provide a biopsy needle that is easier to use and safer to handle. An even further advancement in the art would be to provide the biopsy needle with a marker to alert the physician when the needle has been withdrawn to the maximum withdrawal length prior to reinsertion at a different angle so as to preclude aspiration of air upon complete withdrawal of the biopsy needle from the tissue. Such a novel apparatus and method is disclosed and claimed herein.

BRIEF SUMMARY AND OBJECTS OF THE INVENTION

This invention is an improved biopsy needle and method for obtaining aspirates through fine-needle biopsy. The needle is a conventional hollow needle having a sharpened tip and a fenestrated sidewall. The fenestrations are formed as a plurality of fine holes in the sidewall adjacent the sharpened tip. The needle also includes a marker to provide a visible indication that the fenestrations in the needle are approaching the tissue surface to thereby provide a visible warning of the risk of the loss of negative pressure. An enlarged reservoir in the hub of the needle provides a collection reservoir for aspirate to preclude its being drawn into the syringe. A pair of enlarged wings on each side of the needle hub to increase handling safety and to facilitate attachment and removal of the needle from the syringe.

It is, therefore, a primary object of this invention to provide improvements in fine needle aspiration biopsy needles.

Another object of this invention is to provide improvements in the method of obtaining aspirates using fine needle biopsy.

Another object of this invention is to provide an aspirate that is more representative of the tissue through which the biopsy needle passes by providing a fenestrated needle having a plurality of holes in the sidewall of the biopsy needle adjacent the sharpened tip.

Another object of this invention is to provide a biopsy needle having a fenestrated sidewall, the fenestrations reducing the tendency for coring by the biopsy needle.

Another object of this invention is to provide a marker on the biopsy needle to serve as an indicator when the limit of withdrawal has been reached prior to directing the biopsy needle into the tissue at another preselected orientation to gather a more comprehensive sample from the tissue, the marker serving as a visible warning device to preclude loss of negative pressure through inadvertent exposure of the fenestrations outside the tissue.

Another object of this invention is to provide an enlarged reservoir in the hub of the biopsy needle so as to accommodate the collection of an aspirate in the absence of drawing aspirate into the syringe.

Another object of this invention is to provide a biopsy needle that is easier and safer to handle due to enlarged wings on the hub of the needle, the wings making it easier to attach and remove the needle from the syringe.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

Figure 1:
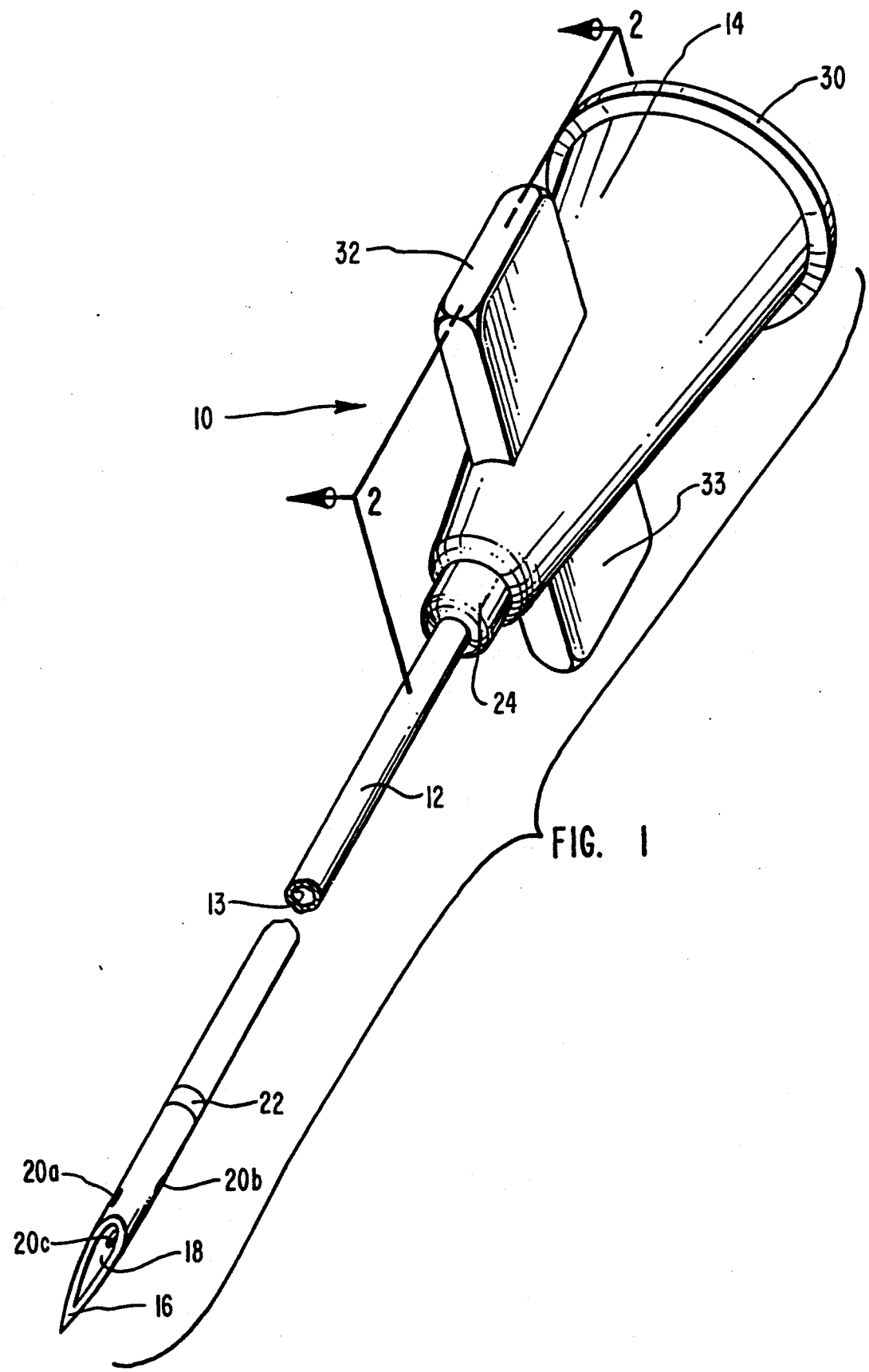
FIG. 1 is an enlarged, perspective view of the novel biopsy needle of this invention shown foreshortened for ease of presentation.

The invention is best understood by the following description with reference to the drawing wherein like parts are designated by like numerals throughout.

GENERAL DISCUSSION

The fenestrated biopsy needle of this invention has proven to be superior for increasing the number of free cells collected from tissue. Further, it was found that the cells collected thereby were more representative of the total tissue mass meaning that the likelihood of a false negative reading was substantially reduced. In one test, a double blind study was undertaken to determine the cell harvesting capability of the fenestrated biopsy needle versus a conventional needle. Both types of needles in the study were operated in an identical manner and under the same negative pressure. The results revealed that the fenestrated needle was 100% successful in harvesting a greater number of free cells than the conventional biopsy needle.

Cell harvest using the novel, fenestrated biopsy needle of this invention is conducted by attaching the needle to a conventional hypodermic syringe. Advantageously, a pair of enlarged wings on each side of the needle hub significantly facilitate handling, removal, and attachment of the hub to the hypodermic syringe. This is important since great care must be taken while working with a sharp object to preclude accidental puncture, particularly in light of the danger of accidental infection by the viral agent responsible for the disease known as AIDS (Acquired Immune Deficiency Syndrome).

The needle is then directed into the tissue at the predetermined angle and to the predetermined depth. A marker on the needle serves as a depth gauge to indicate when the fenestrations in the needle are nearing the surface of the tissue as the needle is being withdrawn. Passage of the marker into the tissue also provides visual indication to the physician that suction can be applied to the needle. Suction is continued during the penetration of the needle to its full depth of penetration as well during withdrawal of the needle until the marker is again visible. The marker allows the physician to change the angular orientation of the needle according to a predetermined pattern without exposing the fenestrations and while simultaneously maintaining negative pressure with the syringe. This means that cells are being harvested continually during the sequences of a) initial and subsequent penetrations; b) partial withdrawals; and, c) through all the changes in the angular orientation of the needle. Prior to exposing the fenestrations during the last withdrawal, the negative pressure in the syringe is released so as to preclude the aspiration of air into the needle.

The fenestrated sidewall of the needle significantly reduces the tendency for the negative pressure inside the needle to create a coring action by the sharpened tip of the needle. In particular, the fenestrations direct a portion of the suction to the sides of the needle where it is used to aid in the harvest of aspirate through the fenestrations.

Aspirate is collected in the reservoir of the enlarged hub during the foregoing cell harvesting procedure. The needle is removed from the syringe so that a saline solution can be drawn into the syringe and used to flush aspirate from the needle after the needle has been remounted on the syringe. Alternatively, the entire assembly of needle and syringe can be forwarded to the pathologist for further processing.

DETAILED DESCRIPTION

Figure 2:
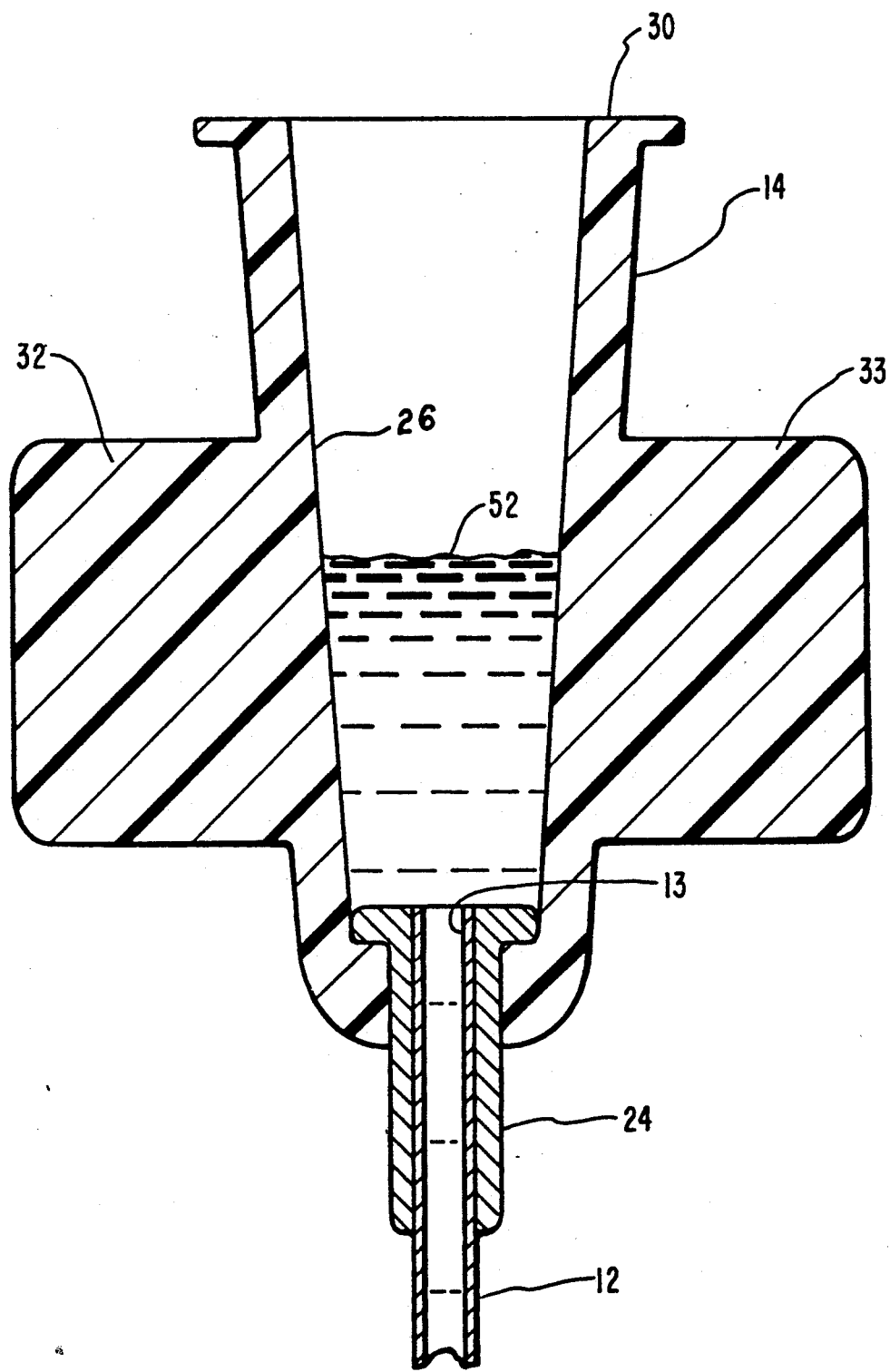
FIG. 2 is an enlarged, partial cross-sectional view taken along lines 2—2 of FIG. 1.

Referring now to FIGS. 1 and 2, the novel biopsy needle of this invention is shown generally at 10 and includes a hollow needle 12 mounted at a proximal end in a needle hub 14. Needle 12 includes a sharpened point 16 at a distal end. Needle 12 is a conventional hollow needle such as a 22 gauge needle having a hollow throughbore 13 and includes an open end 18 adjacent sharpened point 16. Needle 12 is fenestrated with a plurality of holes in its sidewall immediately adjacent sharpened point 16, the holes being shown as fenestrations 20a-20c. Fenestrations 20a-20c are each configured with a diameter incrementally smaller than the inside diameter of needle 12 and are prepared so as to provide a scraping action against tissue 50 (FIG. 3) a will be discussed more fully hereinafter. A visible marker 22 is formed as a distinct band at a position spaced from fenestrations 20a-20c. Marker 22 is designed to provide the physician (not shown) with a visual indication as needle 12 is withdrawn from tissue 50 (FIG. 3) to thereby preclude fenestrations 20a-20c from being inadvertently exposed to the atmosphere.

The proximal end of needle 12 is mounted in a conventional fitting 24 which securely engages needle 12 and adapts it to being mounted in hub 14. Conventionally, needle 12 is fabricated from stainless steel while fitting 24 is fabricated from an aluminum material which can be deformably secured to the proximal end of needle 12 and thereby provide a secure fixation point for needle 12 in hub 14. Hub 14 is fabricated from a suitable, medical grade plastic and is configured with a conventional Luer fitting 30 to adapt hub 14 being releasably mounted to a conventional syringe (not shown). Hub 14 is elongated to provide a reservoir 26 between Luer fitting 30 and needle 12 so as to receive aspirate, shown schematically herein as aspirate 52, retrieved from tissue 50 (FIG. 3) as will be discussed more fully with respect to FIG. 3. Hub 14 also includes a pair of outwardly extending wings 32 and 33 which are designed to enhance finger grasping of hub 14 so as to facilitate removal/attachment of hub 14 to the syringe (not shown).

Figure 3:
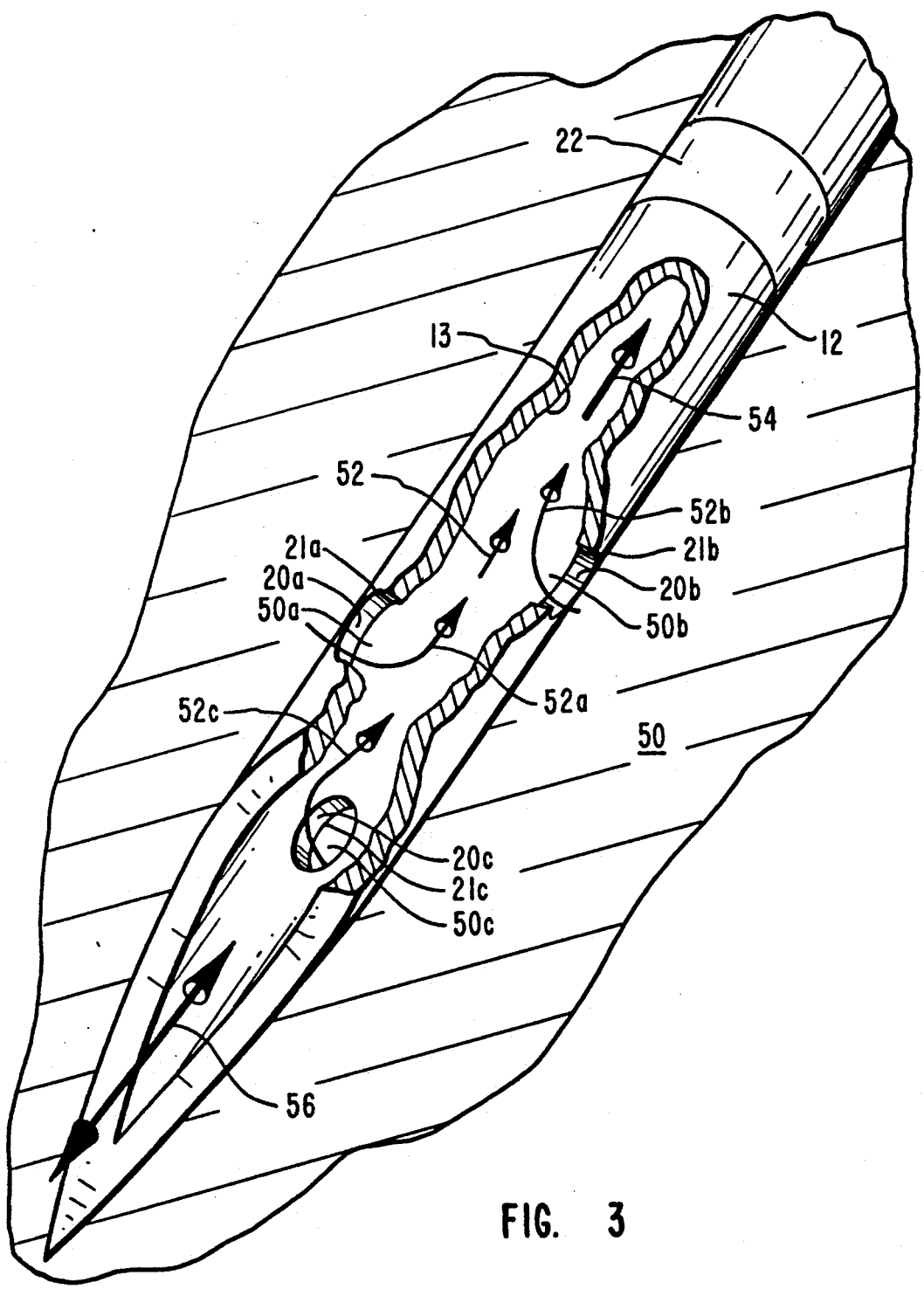
FIG. 3 is an enlarged, schematic, cross-sectional view of a fragmentary portion of the biopsy needle in tissue.

Referring now to FIG. 3, needle 12 is shown greatly enlarged in this fragmentary, cross-sectional view as it resides in tissue 50. Fenestrations 20a-20c, are formed in the sidewall of needle 12 so that negative pressure (indicated schematically at suction arrow 54) inside the hollow throughbore 13 will draw aspirate 52 therethrough and into aspirate reservoir 26 (FIG. 2). Each of fenestrations 20a-20c includes an outer rim 21a-21c, respectively, formed as a sharp ridge circumscribing each of fenestrations 20a-20c, respectively. Suction 54 pulls tissue 50 inwardly into each of fenestrations 20a-20c as protrusions 50a-50c, respectively, while rims 21a-21c, respectively, scrape across the surface of each of protrusions 50a-50c resulting in aspirate samples 52a-52c, respectively, being collected therefrom. Aspirate samples 52a-52c are then drawn as aspirate 52 by suction 54 through throughbore 13 into aspirate reservoir 26 (FIG. 2).

The relatively small diameter of fenestrations 20a-20c are specifically configured to preclude protrusions 50a-50c, respectively, of tissue 50 from excessively protruding into throughbore 13 and thereby blocking suction 54. All known prior art needles, particularly the needle cannulae of the prior art described hereinbefore, suffer from this defect. The importance of continuous collection of aspirate 52 can not be stressed enough since even a momentary interruption in the collection sequence may result in a failure to collect aspirate 52 which contain cells indicative of an abnormal cellular condition. If fenestrations 20a-20c were larger, the known elasticity of tissue 50 would allow protrusions 50a-50c to interfere with suction 54. This is particularly important with respect to fenestration 20b since it is the first opening relative to suction 54 which means that if protrusion 50b were to block suction 54 very little, if any, aspirate 52 would be collected during the period of such blockage.

The direction of traverse of needle 12 in tissue 50 is indicated schematically by double arrow 56, which is shown as a double arrow to indicate that aspirate sample 52 is collected through fenestrations 20a-20c regardless of the direction of travel of needle 12. In particular, the previously described scraping action by rims 22a-22c occurs during each direction of travel of needle 12 whereas a prior art needle (not shown) characterized by the absence of fenestrations 20a-20c will generally not collect sample during the withdrawal phase simply because there is no scraping action during the withdrawal phase.

The Method

Referring now to FIGS. 1-3, the medical professional (not shown) obtains biopsy needle 10 and mounts it on the end of a hypodermic syringe (not shown). Outwardly extending wings 32 and 33 greatly facilitate hand grasping hub 14 and securely engaging hub 14 in mating relationship with the corresponding Luer fitting (not shown) on the hypodermic syringe (not shown). Clearly, of course, biopsy needle 10 can be mounted to any suitable suction device for selectively imposing the predetermined degree of suction 54 inside needle 12. Wings 32 and 33 also provide the necessary leverage for twisting hub 14 to attach and remove the same from the foregoing hypodermic syringe. This is important since hub 14 must be firmly secured in place so as to preclude air leakage into hub 14 during the suction phase of biopsy needle 10. Accordingly, hub 14 is not only firmly mounted in place through the assistance of wings 32 and 33 but wings 32 and 33 also readily assist in the release of hub 14. Importantly, wings 32 and 33 significantly improve the safe handling of biopsy needle 10 in that hub 14 is readily handled, secured and removed in the absence of other tools (not shown) which experience has demonstrated are frequently necessary when using the prior art biopsy needles (not shown).

Needle 12 is then directed into tissue 50 until fenestrations 20a-20c are embedded in tissue 50 at which time suction 54 is imposed on biopsy needle 12. Importantly, marker 22 provides the necessary indicia to indicate when fenestrations 20a-20c are sufficiently embedded within tissue 50 to allow suction 54 to be applied without fear of its loss through inadvertent exposure of fenestrations 20a-20c. With the application of suction 54, aspirate 52 is collected in throughbore 13 and drawn into aspirate reservoir 26.

Aspirate 52 is collected by the scraping action of rims 22a-22c as needle 12 is inserted and withdrawn (arrow 56) through tissue 50 along with the cutting action of sharpened tip 16. Importantly, aspirate 52 is collected during the full distance of traverse by needle 12 in tissue 50. Needle 12 is withdrawn from tissue 50 until marker 22 is visually observed; and, upon observing marker 22, the medical professional (not shown) immediately stops the withdrawal process and reorients needle 12 to a different sector of tissue 50. After reorientation, needle 12 is again forced into tissue 50 to the predetermined depth. At all times during the withdrawal, reorientation, and reentry of needle 12 in tissue 50, suction 54 is maintained in needle 12 so as to continuously collect aspirate 52. This, in turn, assures a continuous "sweeping" of aspirate 52 from all sectors of tissue 50 thereby providing an aspirate 52 that is more representative of the cellular structure of tissue 50. Aspirate 52 is pulled by suction 54 into aspirate reservoir 26 where it collects during the foregoing procedure.

At the conclusion of the sampling probe, suction 54 is discontinued and needle 12 is withdrawn from tissue 50. Biopsy needle 10 is removed from the suction syringe (not shown) by hand grasping hub 14 at wings 32 and 33 and twisting hub 14 to remove hub 14 from its interlocking relationship with the suction syringe (not shown). Advantageously, since the suction syringe (not shown) may be a conventional syringe, it can be charged with a predetermined volume of saline solution and then reattached to hub 14 so as to direct this saline (not shown) through aspirate reservoir 26 flushing aspirate 52 therefrom. Aspirate 52 is transferred to the preselected microscope slide (not shown), culture medium (not shown), or the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A biopsy needle for collecting cells from inside a tissue comprising:
   a hollow hub;
   a hollow needle having a proximal end and an open distal end, the interior of said hollow needle having a first diameter, said hollow needle being mounted at said proximal end to said hollow hub and in fluid communication with said hollow hub;
   suction means for imposing a negative pressure inside said hollow hub and said hollow needle;
   a sharpened point on said hollow needle at said open distal end for penetrating said tissue;
   a plurality of fenestrations in a sidewall of said hollow needle adjacent said distal end, each fenestration comprising a hole having a rim and a second diameter, said second diameter being smaller than said first diameter of said hollow needle; and
   scraper means for scraping cells from said tissue, said scraper means comprising said suction means in combination with said plurality of fenestrations with said rim acting as a scraper for collecting cells from said tissue as said distal end of said hollow needle is inserted and retracted through said tissue with said negative pressure pulling said tissue inwardly into said holes with said rims scraping said cells from said tissue whereby said second diameter of said holes inhibits said tissue from being pulled by said negative pressure into said hollow needle to an extent that it plugs said hollow needle.

2. The biopsy needle defined in claim 1 wherein said hollow hub includes a reservoir means for receiving an aspirate comprising said cells scraped from said tissue into said hollow needle and drawn into said hollow hub through said hollow needle.

3. The biopsy needle defined in claim 1 wherein said hollow hub includes a Luer fitting for releasably mounting said hollow hub to a syringe, said syringe comprising said suction means.

4. The biopsy needle defined in claim 3 wherein said hollow hub includes a pair of outwardly extending wings to facilitate hand manipulation of said hollow hub.

5. The biopsy needle defined in claim 1 wherein said hollow needle includes a marker adjacent said fenestrations at said distal end, said marker being located between said fenestrations and said hollow hub, said marker providing a visual indication of the withdrawal limit for said biopsy needle.

6. A biopsy needle system for collecting cells from tissue comprising:
   a hollow hub, said hollow hub including a Luer fitting;
   a syringe releasably mountable to said hollow hub with said Luer fitting, said syringe comprising a suction means for imposing a suction in said hollow hub;
   a hollow needle having a first, internal diameter and a proximal end and an open distal end, said hollow needle including a sharpened point at said open distal end to enable said needle to penetrate said tissue, said hollow needle being mounted at said proximal end to said hollow hub and in fluid communication with said hollow hub to transmit said suction into said hollow needle;
   a plurality of fenestrations in said hollow needle adjacent said distal end adjacent said sharpened point, said fenestrations comprising a plurality of holes, each hole having a second diameter and a rim, said rims acting in combination with said suction means as scraper means for collecting cells from said tissue as said distal end of said hollow needle is inserted into said tissue while said suction if pulling said tissue into said hollow needle through said holes with said rims scraping cells from said tissue; and
   means for inhibiting plugging of said hollow needle with said tissue comprising said second diameter being smaller than said first diameter thereby precluding tissue drawn by said suction through said holes from plugging said hollow needle.

7. The biopsy needle defined in claim 6 wherein said hollow hub includes outwardly extending engagement means for facilitating engagement of said hollow hub.

8. The biopsy needle defined in claim 7 wherein said engagement means comprises a pair of wings, said wings being configured to enhance hand-grasping and twisting said hollow hub.

9. The biopsy needle defined in claim 6 wherein said hollow hub includes a reservoir means for receiving aspirate drawn into said hollow hub through said hollow needle.

10. The biopsy needle defined in claim 6 wherein said hollow needle includes a marker adjacent said fenestrations at said distal end, said marker being located between said fenestrations and said hollow hub, said marker providing an indication of a withdrawal limit for said fenestrations to preclude inadvertently exposing said fenestrations.

11. A method for obtaining a biopsy sample from tissue using a hollow needle comprising:

preparing a hollow hub, said hollow hub being releasably mountable to a suction means;

mounting a hollow needle to said hollow hub at a proximal end of said hollow needle, said hollow needle having a first, internal diameter and a sharpened point at an open distal end;

forming a scraper means at said distal end of said needle for scraping cells from said tissue, said scraper means comprising a plurality of fenestrations in said hollow needle, said fenestrations comprising a plurality of holes in a sidewall of said hollow needle, each hole having a second diameter and a rim with said rims cooperating with a suction thereby scraping cells from said tissue;

inserting said hollow needle into said tissue by puncturing said tissue with said sharpened point;

applying said suction to said hollow needle while said hollow needle is directed through said tissue, said scraper means collecting said biopsy sample from said tissue with said suction drawing said biopsy sample through said fenestrations and through said hollow needle into said hollow hub; and precluding plugging of said hollow needle with tissue by forming said second diameter smaller than said first diameter thereby preventing tissue from protruding through said fenestrations into and plugging said hollow needle.

12. The method defined in claim 11 wherein said preparing step includes forming a reservoir in said hollow hub, said reservoir receiving said biopsy sample.

13. The method defined in claim 11 wherein said preparing step includes mounting a pair of outwardly extending wings on said hollow hub, said wings improving handling characteristics of said hollow hub particularly during mounting and removing said hollow hub relative to said suction means.

14. The method defined in claim 11 wherein said forming step includes placing a marker on said hollow needle adjacent said fenestrations with said marker between said fenestrations and said hollow hub, said marker providing a visible indicator as a warning that said fenestrations are near the surface of said tissue.

* * * * *